United States Patent

Hubbard et al.

Patent Number: 5,109,841
Date of Patent: May 5, 1992

[54] FACIAL ICE PACK

[75] Inventors: Vance M. Hubbard; Welton K. Brunson, both of Bedford, Tex.

[73] Assignee: Tecnol, Inc., N. Richland Hills, Tex.

[21] Appl. No.: 551,911

[22] Filed: Jul. 11, 1990

[51] Int. Cl.$^5$ ................................................ A61F 7/10
[52] U.S. Cl. ..................................... 128/380; 128/402
[58] Field of Search ............... 128/380, 399, 402, 403, 128/400, 82.1; 62/530; 383/901

[56] References Cited

U.S. PATENT DOCUMENTS

| | | | |
|---|---|---|---|
| 1,964,655 | 6/1934 | Williamson | 128/402 |
| 3,491,761 | 1/1970 | Baker | 128/402 |
| 4,044,773 | 8/1977 | Baldwin | 128/403 |
| 4,190,054 | 2/1980 | Brennan | 128/402 |
| 4,326,533 | 4/1982 | Henderson | 128/403 |
| 4,347,848 | 9/1982 | Hubbard et al. | 128/402 |
| 4,523,353 | 6/1985 | Hubbard et al. | 24/30.5 |
| 4,527,566 | 7/1985 | Abare | 128/403 |
| 4,688,572 | 8/1987 | Hubbard et al. | 128/402 |
| 4,805,620 | 2/1989 | Meistrell | 128/403 |
| 4,835,950 | 5/1983 | Hubbard et al. | 156/73.1 |

OTHER PUBLICATIONS

"Omnipak" (Advertisement) 6/82.

Primary Examiner—Edward M. Coven
Assistant Examiner—Mark S. Graham
Attorney, Agent, or Firm—Baker & Botts

[57] ABSTRACT

An ice pack is provided which comprises a waterproof envelope having a first and second side, and further having a sealable open end and a closed end. A strap is attached at one end to the waterproof envelope and has a centrally disposed longitudinal slit. A fastener is in turn attached to the free end of the strap, and is fastenable to an outer surface of the waterproof envelope.

22 Claims, 3 Drawing Sheets

FACIAL ICE PACK

TECHNICAL FIELD OF THE INVENTION

This invention relates generally to the field of medical devices, and more particularly to a facial ice pack.

BACKGROUND OF THE INVENTION

Ice packs for single patient use are generally of two types: large general purpose ice packs designed for application to large areas of the body and small, specialized ice packs designed for cold application at particular points.

Impaction injuries to the face, in the jaw and cheek areas, for example, require an ice pack application to chill the affected area in order to reduce swelling and to prevent pain and further tissue damage. Because the human head is generally spherical in shape, it is therefore one of the most difficult body parts on which to apply medical dressings such as ice packs. Accordingly, a need has arisen to provide for an ice pack which can be secured to the head to apply a cold application directly to an injured facial area.

Because of the proximity of the injured area to the eyes, nose and mouth, it is important that the ice pack application does not interfere with their functions, such as sight, respiration, speech and eating. Accordingly, it is further desirable to provide for an ice pack which may be fastened to the head securely and yet in an unobstructive manner.

The present invention provides for a facial ice pack and is directed to overcoming one or more of the problems as set forth above.

SUMMARY OF THE INVENTION

The facial ice pack, in accordance with the present invention, may be applied to injured facial areas to reduce swelling and pain, and to prevent further tissue damage. The ice pack of the present invention can be worn around a patient's head securely and without covering the eyes, nose and mouth.

In accordance with one aspect of the present invention, an ice pack is provided which comprises a waterproof envelope having a first and second side, and further having a sealable open end and a closed end. One end of a strap is attached to the waterproof envelope. The strap has a centrally disposed longitudinal slit. A fastener is attached to the free end of the strap, and is fastenable to an outer surface of the waterproof envelope.

Another aspect of the present invention comprises a first waterproof envelope and a second waterproof envelope. Both waterproof envelopes have first and second sides and open and closed ends. The waterproof envelopes are attached to one another at their closed ends. One end of a strap is attached to the second waterproof envelope and has a centrally disposed longitudinal slit. Additionally, a fastener is attached to the free end of the strap and is engageable with the outer surface of the first waterproof envelope.

BRIEF DESCRIPTION OF THE DRAWINGS

For a better understanding of the present invention, references may be made to the accompanying drawings, in which.

DETAILED DESCRIPTION OF THE INVENTION

The application of the present invention is best understood by referring to FIGS. 1A, 1B, 1C and 1D. A preferred embodiment of a unilateral facial ice pack 10 of the present invention is shown being worn by a patient in FIGS. 1A and 1B. Ice pack 10 is applicable to facial injuries, such as on the cheek or jaw areas, to reduce swelling and further tissue damage. Note that unilateral facial ice pack 10, when applied to facial injuries, does not interfere with the patient's ability to see, breathe, speak or eat. Therefore, facial ice pack 10 is designed to be applied in an unobstructive manner.

Figure 1A:
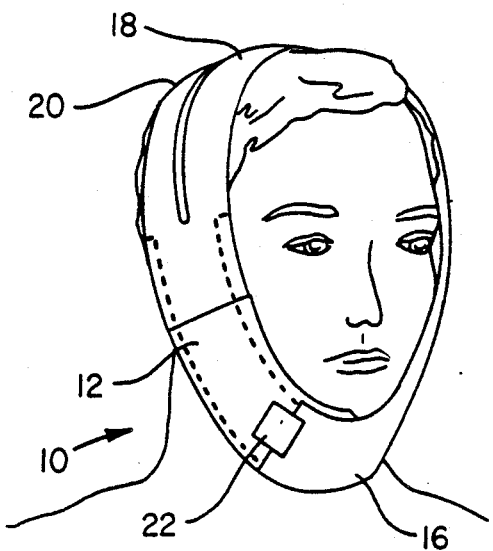
FIG. 1A is a perspective view of the facial ice pack applied to the head of a patient.
Figure 1B:
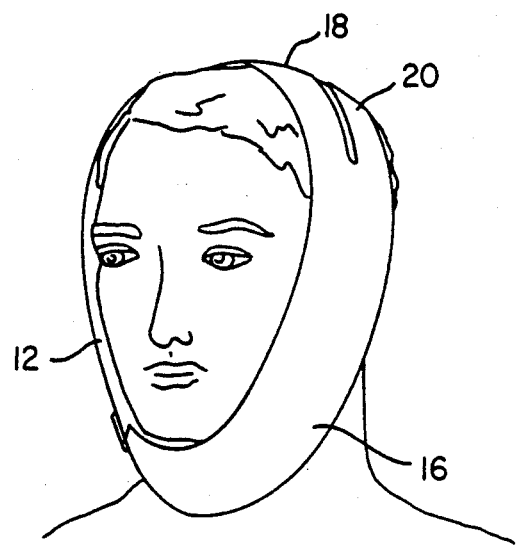
FIG. 1B is another perspective view of the facial ice pack.

To clearly illustrate the manner in which unilateral ice pack 10 may be applied to facial injuries, FIG. 1A and 1B show the patient from the front right and front left sides, respectively. Unilateral ice pack 10 includes an ice compartment 12 which is held proximate to the cheek and jaw of the patient by a strap 16 attached to ice compartment 12 at one end. Strap 16 includes a centrally located longitudinal slit that divides strap 16 into two narrower strips 18 and 20, which substantially follow the contour of the patient's head and hold unilateral ice pack 10 in place. A fastening tab 22 constructed of hook-like material is attached to the free end of strap 16 and is engageable with the outer surface of ice compartment 12, which is covered with a loop-like material.

Figure 1D:
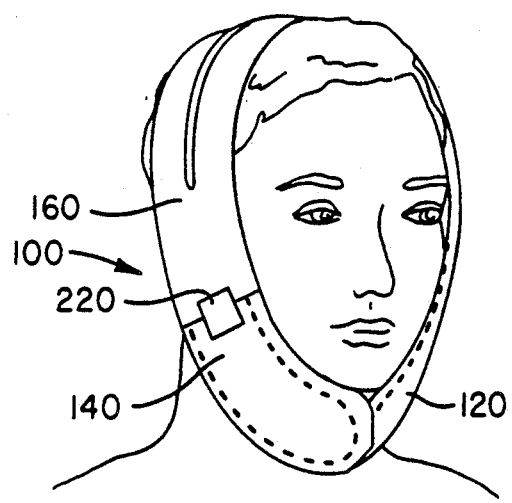
FIG. 1D is another perspective view of the facial ice pack showing a tab fastened to the body of the ice pack.
Figure 1C:
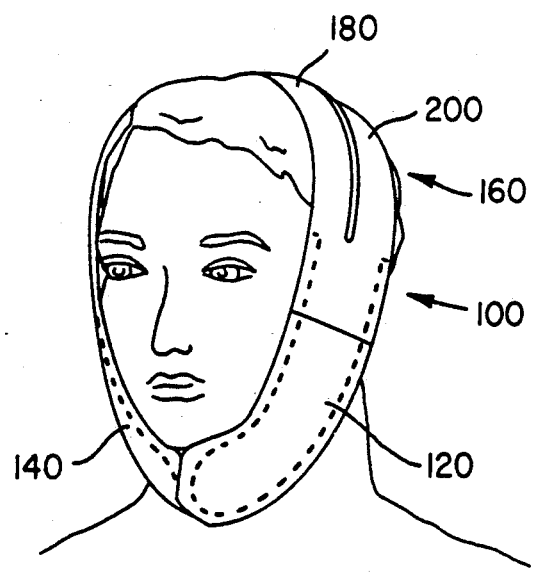
FIG. 1C is a perspective view of a further embodiment of the facial ice pack applied to the head of a patient.

An alternate embodiment of the present invention is a bilateral ice pack 100 shown in FIGS. 1C and 1D being worn by a patient. Bilateral ice pack 100 is substantially similar to unilateral ice pack 10, but has two ice compartments, so that injuries to both cheeks and jaws of the patient may be chilled by the same apparatus 100.

FIGS. 1C and 1D show the front right and front left sides of the patient in order to clearly illustrate the manner in which bilateral ice pack 100 may be worn. Bilateral ice pack 100 includes ice compartments 120 and 140 and is worn with them adjacent to the cheeks and jaws of the patient. Similar to the construction of unilateral ice pack 10, a strap 160 is attached to one end of ice compartment 120, which may be used to wrap around the top and back of the patient's head. Strap 160 further includes a central longitudinal slit that divides strap 160 into narrower strips 180 and 200. A hook-like fastening tab is attached to the end of strap 160, which is engageable with the outer surface of ice compartment 140.

Figure 2:
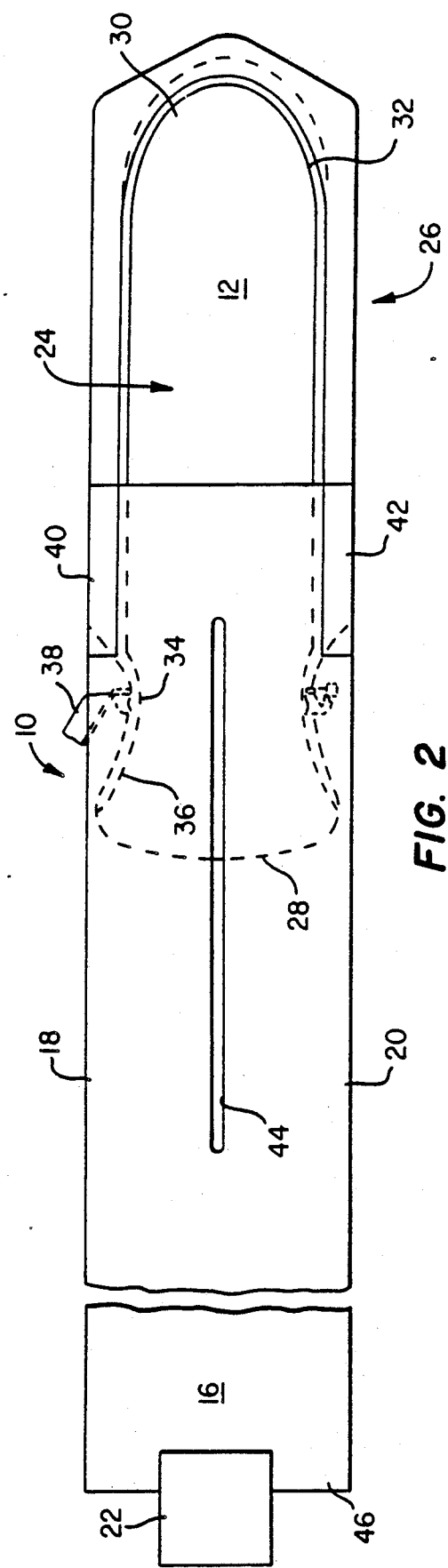
FIG. 2 is a plan view of an embodiment of the facial ice pack.

FIG. 2 shows a more detailed depiction of a preferred embodiment which is constructed in accordance with the present invention. Shown in FIG. 2 is the unilateral embodiment of the present invention. Unilateral facial ice pack 10 includes a generally rectangular envelope or bag 12 constructed of waterproof material, such as polyethylene or other inexpensive waterproof material. Two pieces of waterproof material are bonded and sealed to form sides 24 and 26, an open end 28 and a closed end 30. As shown in FIG. 2, waterproof envelope 12 is formed internally of ice pack 10 by sealing along its edges as indicated by a broken line 32. Envelope 12 preferably has a narrowing throat 34 and a widening opening 36, but may be constructed without aforesaid features. Further details of the construction of ice pack 10 are set forth in U.S. Pat. No. 4,347,848 issued to Hubbard et al. A closure member 38, such as the one set forth in U.S. Pat. No. 4,523,353 also issued to Hubbard et al., may be used to seal open end 28 to prevent spillage of ice. Details of ice pack 10 and closure member 38 may be obtained by referring to the above-referenced patents and will not be discussed herein.

Strap 16 is attached in the proximity of open end 28 of waterproof envelope 12 by bonding envelope material and strap 16 at areas 40 and 42. Strap 16 further extends substantially longitudinally from waterproof envelope 12. Strap 16 is preferably constructed of a pliable and durable material of light weight. Because strap 16 comes in contact with the patient's skin, it should feel soft and comfortable to the touch. As described previously, strap 16 has a centrally located longitudinal slit 44 which divides strap 16 into two narrower strips 18 and 20. Slit 44 is preferably positioned on strap 16 so that when ice pack 10 is worn by a patient, strips 18 and 20 follow the contour of the patient's head to hold ice pack 10 securely in place without sliding or slipping. It should be obvious that the length of strap 16 is such that it allows ice pack 10 to be comfortably worn around a patient's head in the manner shown in FIGS. 1A and 1B.

Fastening tab 22 is attached to free end 46 of strap 16 and is constructed of a hook-like material. When in contact with a loop-like material under minimum pressure, the "hooks" on fastening tab 22 engage the "loops" and form a substantially secure bond. Such loop-like material is bonded to side 24 of waterproof envelope 12 also along seam 32, so that side 24 is substantially covered therewith. Constructed in this manner, ice pack 10 may be secured to a patient's head by pressing fastening tab 22 onto any area of side 24, thereby making the effective length of strap 16 adjustable.

Unilateral facial ice pack 10 is useful when the patient's facial injury is treatable with the surface area of one ice compartment 12, such as injury to only one side of the face. In the event the patient suffered from injuries to both sides of the face, a bilateral construction of the facial ice pack may be used to cool the injured area to prevent swelling and lessen pain.

Figure 3:
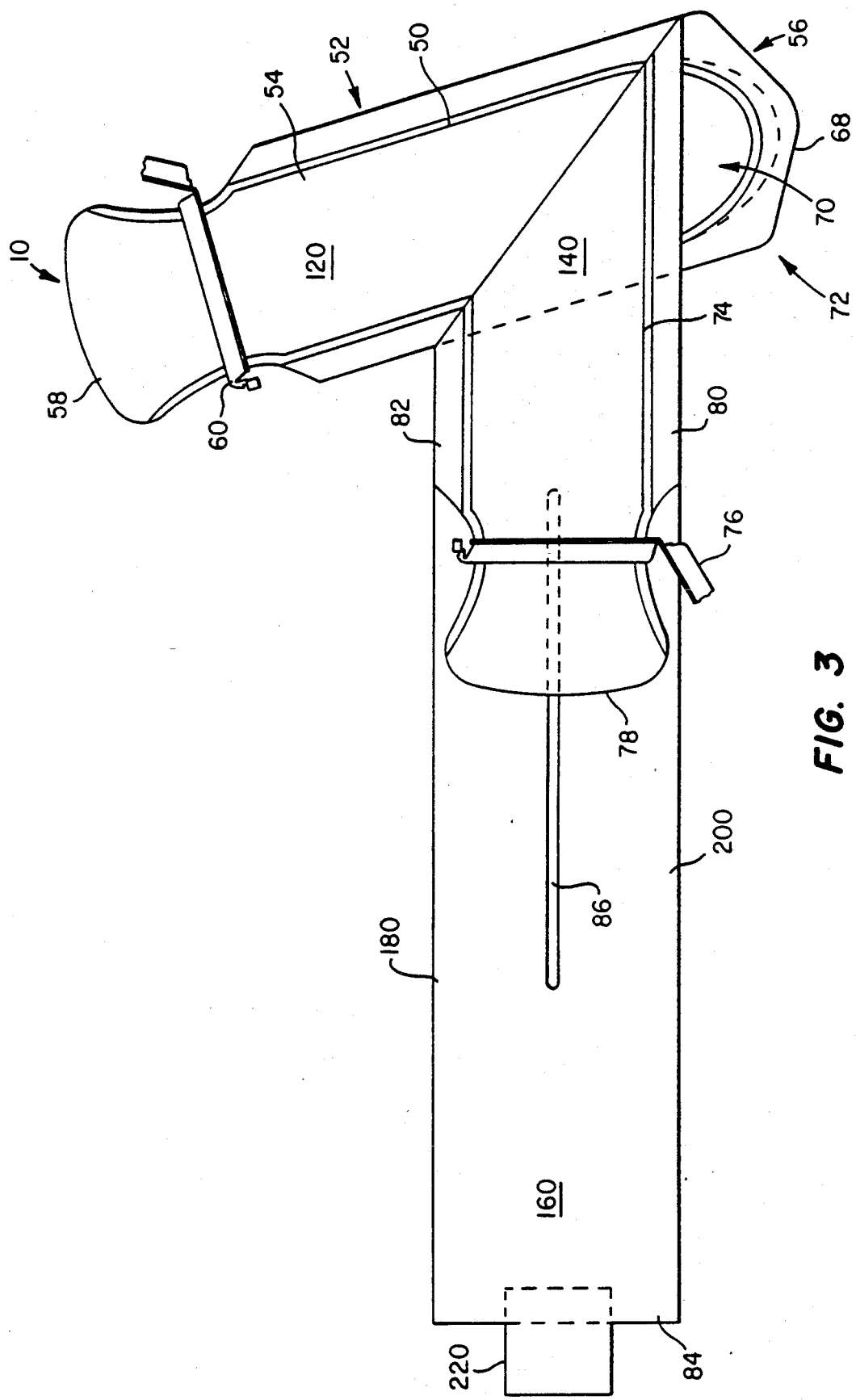
FIG. 3 is a plan view of an alternate embodiment of the facial ice pack.

Referring to FIG. 3, the bilateral embodiment of a facial ice pack is shown. The notable difference between unilateral ice pack 10 and bilateral ice pack 100 is the addition of a second waterproof envelope 140. Envelope 120 of bilateral ice pack 100 is similar to waterproof envelope 12 of the unilateral construction. Envelope 120, made of waterproof material, is formed internally by bonding and sealing two pieces of waterproof material together along seam 50 and forming side walls 52 and 54. The bonding area is indicated by a dotted portion along seam 50 at the edges of waterproof envelope 120. A closed end 56 and an open end 58 of envelope 140 are thus formed, and open end 58 may be sealed shut by a closure member 60. Side 52 of waterproof envelope 120 is further covered with a loop-like material engageable by a fastening tab 220, which is attached to a strap 160 on a second waterproof envelope 140.

A second waterproof envelope 140 is attached proximate to closed end 56 of waterproof envelope 120 by bonding a portion, indicated at 68, of the material of respective envelopes 120 and 140. It is important to note that although waterproof envelope 120 is shown positioned transversely at an angle to waterproof envelope 140, waterproof envelopes 120 and 140 are substantially aligned longitudinally with one another. Second waterproof envelope 140 also has two side walls 70 and 72, with side 70 being adjacent to side 54 of waterproof envelope 12. Envelope 149 is also formed by bonding two pieces of waterproof material along the edges, as indicated by seam 74. A closure member 76, like closure member 60 of envelope 120, is arranged to seal off an open end 78 of envelope 140. A strap 160 is attached to waterproof envelope 140 at areas generally indicated at 80 and 82. At a free end 84 of strap 160, a fastening tab 220 is attached thereto. Fastening tab 220 is constructed from a hook-like material. Strap 160 also includes a centrally located longitudinal slit 86. The length of strap 16 and the relative location of slit 86 thereon are such that when bilateral ice pack 100 is worn around a patient's head in the manner shown in FIGS. 1C and 1D, narrower strips 180 and 200 formed by slit 86 follow the contour of the patient's head to prevent slippage. Constructed in this manner, bilateral facial ice pack 100 may be fastened around the head and chin of a patient by pressing fastening tab 220 onto any portion of side 52 of waterproof envelope 120.

Figure 4:
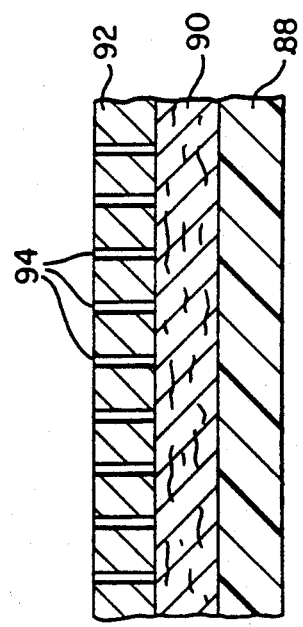
FIG. 4 is a magnified sectional view of the preferred material from which the ice pack is constructed.

FIG. 4 shows a magnified cross section of the preferred material and construction of waterproof envelopes 12, 120 and 140. The innermost layer of material is a thin sheet of polyethylene 88, which is waterproof and retains ice and water. Layer 88 is bonded to an intermediate layer 90 of absorbent material, which in turn is bonded to an outer layer of absorbent material 92. Layer 92 has a multitude of pores or holes 94 which permit condensed moisture to evaporate from the interface of layers 88 and 90. Rayon polyester fiber provides a suitable absorbent material for use in this application. The material layers 88, 90 and 92 may be bonded together by ultrasonic welding as known in the art. The above material construction is used to form side 26 of envelope 12 of unilateral facial ice pack 10 shown in FIG. 2 and side 54 of envelope 120 and sides 70 and 72 of envelope 140 of bilateral facial ice pack 100 shown in FIG. 3.

Figure 5:
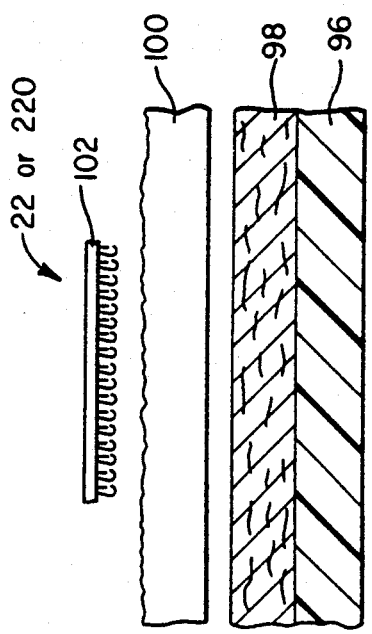
FIG. 5 is another magnified sectional view of the preferred ice pack material, the showing the hook and loop fastener.

FIG. 5 shows another magnified cross section of the material layers with the hook and loop fastener material layer used for side 24 of envelope 12 of unilateral facial ice pack 10 and side 52 of envelope 120 of bilateral facial ice pack 100. An inner layer 96 is constructed of a thin polyethylene material which retains ice and water. An intermediate layer 98 constructed of an absorbent and pliable material like that of layer 90 of FIG. 4 is bonded to layer 96. An outer layer 100, which may be absorbent constructed of loop-like material, such as brushed pile, is laid on top of layers 96 and 98 and welded thereto at the outer edges as described above. The porous characteristic of material layer 100 enables it to function like material layer 92, which permits an evaporation of condensed moisture in addition to allowing fastening tab 22 or 220, made of a hook-like material 102, to engage it with an application of minimum pressure.

Although the present invention has been described in detail, it should be understood that various changes, substitutions and alterations can be made thereto without departing from the spirit and scope of the invention as defined by the appended claims.

What is claimed is:

1. An ice pack, comprising:
    a waterproof envelope having a first and second side, and having an open end and a closed end, said open end being sealable;
    a strap having a centrally disposed longitudinal slit, said strap having a free end and a second end attached to said waterproof envelope proximate said open end, and extending longitudinally therefrom;
    fastening means for connecting said strap to said waterproof envelope; and
    wherein said first side of said waterproof envelope is constructed of an inner waterproof material layer, an intermediate absorbent material layer, and an outer pressure responsive fastening material layer.

2. The ice pack, as set forth in claim 2, wherein said fastening means is attached to said strap and is engageably fastenable to said pressure responsive fastening material on said outer surface of said waterproof envelope.

3. The ice pack, as set forth in claim 2, wherein said fastening means is attached to said strap and has hook-like elements engageable and disengageable with said pressure responsive material on outer surface of said waterproof envelope.

4. The ice pack, as set forth in claim 1, wherein said second side of said waterproof envelope is constructed of an inner waterproof material layer, an intermediate absorbent material layer, and an outer porous absorbent material layer.

5. The ice pack, as set forth in claim 1, wherein said waterproof envelope and said strap are extendably circumscribable around the top of the head and the chin of a patient.

6. The ice pack, as set forth in claim 5, wherein said slit on said strap is arranged to be positioned substantially on the top of the head of said patient and said waterproof envelope is arranged to be positioned substantially proximate the cheek and jaw of said patient.

7. The ice pack, as set forth in claim 5, wherein said strap is constructed of a pliable, porous and absorbent material.

8. The ice pack, as set forth in claim 5, wherein said open end of said waterproof envelope is resealable.

9. A facial ice pack wrappable around the top of the head and the chin of a patient, comprising:
    a generally rectangular waterproof bag for holding ice, said bag constructed from a multiple ply material and defining an open end and a closed end disposed longitudinally from said open end;
    a pressure responsive fastening material securely disposed on an outer surface of said waterproof bag;
    a strap having a centrally disposed longitudinal slit, said strap having a free end and a second end attached to said waterproof bag proximate said open end and extending longitudinally therefrom;
    a fastening tab on said free end of said strap and engageably fastenable to said pressure responsive fastening material on said outer surface of said waterproof bag; and
    wherein said waterproof bag multiple ply material includes an inner waterproof material layer and an intermediate absorbent material layer.

10. The ice pack, as set forth in claim 9, wherein said waterproof bag multiple material includes the inner waterproof material layer, the intermediate absorbent material layer, and an outer porous absorbent material layer.

11. The ice pack, as set forth in claim 9, said waterproof bag further having first and second sides, wherein said first side is constructed from the inner waterproof material layer bonded to the intermediate absorbent material layer, and an outer pressure responsive fastening material layer, said second side of said waterproof bag being constructed from the inner waterproof material layer bonded to the intermediate absorbent material layer, and an outer porous absorbent material layer bonded to said inner and intermediate layers.

12. The ice pack, as set forth in claim 9, wherein said fastening tab has hook-like elements engageable and disengageable with said pressure responsive material on the outer surface of said first said first of said waterproof bag.

13. The ice pack, as set forth in claim 9, wherein said strap is constructed of a pliable, porous and absorbent material.

14. The ice pack, as set forth in claim 9, wherein said open end of said waterproof bag is sealable and resealable.

15. The ice pack, as set forth in claim 11, wherein said slit on said strap is arranged to be positioned substantially on the top of the head of said patient.

16. An ice pack, comprising:
    a first waterproof envelope having first and second sides and further having an open end and a closed end, said open end being sealable;
    a second waterproof envelope having first and second sides and further having an open end and a closed end, said open end being sealable;
    a strap having a centrally disposed longitudinal slit, said strap having a free end and a second end attached to said second waterproof envelope proximate its said open end and extending longitudinally therefrom;
    fastening means for coupling said strap and said first waterproof envelope; and
    wherein said first side of said first waterproof envelope is constructed of an inner waterproof material layer, an intermediate absorbent material layer and an outer layer of said pressure responsive fastening material, and said second side of said first waterproof envelope is constructed of an inner waterproof material layer, an intermediate absorbent material layer and an outer porous absorbent material layer.

17. The ice pack, as set forth in claim 16, wherein said fastening means is attached to said strap and has hooklike elements engageable and disengageable with said pressure responsive material on said first side of said first waterproof envelope.

18. The ice pack, as set forth in claim 16, wherein said first and second sides of said second waterproof envelope are both constructed of an inner waterproof material layer, an intermediate absorbent material layer, and an outer porous absorbent material layer.

19. The ice pack, as set forth claim 16, wherein said first and second waterproof envelopes and said strap are extendably circumscribably wrappable around the top of the head and chin of a patient, said fastening means on said strap engaging said outer surface of said first side of said first waterproof envelope for securing said ice pack in position.

20. The ice pack, as set forth in claim 19, wherein said first and second waterproof envelopes are arranged to be positioned substantially proximate the cheeks and jaws of said patient, and said slit on said strap is arranged to be positioned substantially on the top of the head of said patient.

21. The ice pack, as set forth in claim 16, wherein said strap is constructed of a pliable, porous and absorbent material.

22. The ice set forth in claim 16, wherein said open end of said second envelope is resealable.

* * * * *

UNITED STATES PATENT AND TRADEMARK OFFICE
CERTIFICATE OF CORRECTION

PATENT NO. : 5,109,841
DATED : May 5, 1992
INVENTOR(S) : Vance M. Hubbard et al.

It is certified that error appears in the above-identified patent and that said Letters Patent is hereby corrected as shown below:

Column 2, line 16, after "material" delete "the".

Column 4, line 18, after "Envelope" second occurrence, delete "149" and insert -- 140 --.

Col. 5, claim 2, line 24, after "claim" delete "2" and insert --1--

Column 4, line 63, after "absorbent" insert -- , --.

Col. 6, claim 12, line 22, after "first" (1st occurrence), delete "said first" and insert --side--.

Col. 6, claim 19, line 66, after "forth" insert --in--

Col. 8, claim 22, line 1, after "ice" insert --pack, as --

Col. 8, claim 22, line 7, after "second" insert --waterproof--.

Signed and Sealed this

Fifth Day of October, 1993

*Attest:*

BRUCE LEHMAN

*Attesting Officer*     Commissioner of Patents and Trademarks